United States Patent
McKay

(10) Patent No.: US 7,955,301 B1
(45) Date of Patent: Jun. 7, 2011

(54) INJECTION SHUT OFF VALVE WITH PRESSURE ACTUATOR FOR DELIVERY OF COMPOSITIONS

(75) Inventor: William F. McKay, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 0 days.

(21) Appl. No.: 12/694,329

(22) Filed: Jan. 27, 2010

(51) Int. Cl.
*A61M 1/00* (2006.01)

(52) U.S. Cl. ........ 604/121; 604/236; 604/256; 604/323; 604/335; 137/517; 137/528; 137/535

(58) Field of Classification Search .................. 604/121, 604/236, 167.01, 167.03, 247, 249, 256–260, 604/323–324, 335, 350; 137/511, 517, 843, 137/528, 535, 540; 251/331
See application file for complete search history.

(56) References Cited

U.S. PATENT DOCUMENTS

| | | | |
|---|---|---|---|
| 4,044,989 A * | 8/1977 | Basel et al. ................ 251/7 |
| 4,516,593 A * | 5/1985 | Muto .................. 137/15.14 |
| 4,819,684 A | 4/1989 | Zaugg et al. |
| 5,163,904 A | 11/1992 | Lampropoulos et al. |
| 5,571,882 A | 11/1996 | Vetter |
| 5,902,273 A | 5/1999 | Yang et al. |
| 6,063,057 A | 5/2000 | Choh |
| 6,616,946 B1 | 9/2003 | Meier et al. |
| 6,652,883 B2 | 11/2003 | Goupil et al. |
| 6,676,971 B2 | 1/2004 | Goupil et al. |
| 6,710,126 B1 | 3/2004 | Hirt et al. |
| 6,723,814 B2 | 4/2004 | Meier et al. |
| 6,869,426 B2 | 3/2005 | Ganem |
| 6,916,308 B2 | 7/2005 | Dixon et al. |
| 7,070,809 B2 | 7/2006 | Goupil et al. |
| 7,302,960 B2 | 12/2007 | Patzer |
| 7,357,792 B2 | 4/2008 | Newton et al. |
| 7,585,280 B2 | 9/2009 | Wilson et al. |
| 7,618,370 B2 | 11/2009 | Choi et al. |
| 7,637,279 B2 | 12/2009 | Amley et al. |
| 2003/0009235 A1 | 1/2003 | Manrique et al. |
| 2005/0287218 A1 | 12/2005 | Chaouk et al. |
| 2005/0288789 A1 | 12/2005 | Chaouk et al. |

* cited by examiner

*Primary Examiner* — Nicholas D Lucchesi
*Assistant Examiner* — Quynh-Nhu H Vu

(57) ABSTRACT

Injection shut off valve devices and methods are provided for limiting flow and pressure from a pharmaceutical composition on injection. In some embodiments, the injection shut off valve is coupled to a syringe and can be used to monitor and avoid maximum pressures that can cause damage on injection.

25 Claims, 5 Drawing Sheets

INJECTION SHUT OFF VALVE WITH PRESSURE ACTUATOR FOR DELIVERY OF COMPOSITIONS

BACKGROUND

During the course of medical treatment, it is often necessary to deliver pharmaceutical compositions (e.g., tissue bulking materials, bone fillers, contrast agents, drugs, growth factors, etc.) to a target tissue site by injection. In general, a hollow needle or cannula with a syringe attached to it is inserted at or near the target tissue and the pharmaceutical composition delivered. At the time of injection, pressure is exerted in the syringe to expel the pharmaceutical composition at or near the target tissue site.

Sometimes, particularly with viscous compositions, such as for example, in situ setting materials, gels, bone cements, and other pharmaceutical compositions, the practitioner will exert excessive pressure to expel the pharmaceutical composition from the needle or cannula. This excessive pressure may rupture the target tissue causing damage to the tissue and/or leakage of beneficial physiological fluid. For example, when treating a spinal disc annular tear or herniation, the practitioner will often administer an in situ setting material at or near the site of the disc injury. If the in situ setting material is administered under excessive pressure, this can cause further trauma to the disc area by causing the nucleus pulposus (the jelly-like substance in the middle of the spinal disc) to leak out of the annulus fibrosus (the fibrous ring of the intervertebral disc) leading to further annulus tearing or herniation and/or painful debilitating effects on the patient by compressing the spinal canal and the spinal nerve root.

The pain from the annular tear or herniated disc may be further exacerbated as the nucleus pulposus contains significant amounts of substances capable of exciting, or increasing the excitability of, sensory nerves such as prostaglandin E, histamine-like substances, lactic acid and polypeptide amines. These substances may also escape increasing the lower back pain or cause radiating leg pain. In addition, the increased pressure from the injection may increase the size of any annular tear present in the disc, which may cause fibrous tissue to grow into the tear, which also increases pain and/or inflammation.

Excessively high pressure injections can damage other tissues such as blood vessels causing blood and/or the pharmaceutical composition to leak into surrounding tissues that are not intended to be the target of the therapy. This may also cause pain, inflammation, edema, scars and often times, necrosis of the surrounding tissue or even an embolism.

High pressure injections may also lead to the practitioner giving too much of the pharmaceutical composition too soon which can be detrimental to the patient due to adverse effects of the sudden dose of the pharmaceutical composition. For example, sudden administration of pharmaceutical compositions can cause fluid overload at or near the target tissue site, which may cause edema, hypertension, electrolyte imbalance, or in severe case heart failure. This is particularly so when administering very potent pharmaceutical compositions that have a low therapeutic index, even small quantities administered too soon to the patient can be detrimental.

Sometimes, if too much pressure is used to expel the pharmaceutical composition from the syringe, the composition may migrate away from the target tissue site leading to reduced efficacy of the composition or even damage to surrounding tissue. For example, when using bone cements or fillers that are administered in a flowable state and later harden after administering them at a target tissue site, if the bone cement or filler is expelled from the needle or cannula at an excessive pressure, it may migrate to surrounding tissue and harden in the wrong area (e.g., such as a healthy joint or vertebrae) which may severely inhibit movement of the joint. In more severe cases, the bone cements or fillers may migrate to a blood vessel and cause an ischemic event (e.g., embolism, necrosis, edema, infarction, etc.), which could be detrimental to the patient.

In light of this background, there exist needs for improved devices and methods for injecting pharmaceutical compositions at or near a target tissue site.

SUMMARY

Devices and methods are provided that allow delivery of the pharmaceutical composition (e.g., tissue bulking materials, bone cements, fillers, contrast agents, drugs, growth factors, etc.) at or near a target tissue site without exceeding a maximum pressure that can cause damage to tissue at or near the target tissue site. One advantage of the embodiments provided herein is that by utilizing an injection shut off valve that prevents flow of the pharmaceutical composition when a maximum pressure is reached, the practitioner can administer the composition where the risk of damage to the tissue resulting from high pressure injections is reduced or eliminated. Another advantage of the devices and methods of the present application is that accurate doses of the pharmaceutical composition can be delivered via injection.

In one embodiment, an injection shut off valve for limiting flow of a composition is provided, the shut off valve comprising: a housing having an inlet, an outlet and a flow path disposed therebetween and in fluid communication with the inlet and the outlet, the inlet configured to receive an end of an injection syringe; and a valve assembly contacting the flow path and having a first chamber and a second chamber, the first chamber comprising a diaphragm movable in at least a closed position to prevent flow of the composition to the outlet, the second chamber having an actuator disposed therein, the actuator responsive to pressure in the flow path and coupled to the diaphragm in the first chamber, the actuator movable in at least an upper position when a select pressure is reached in the flow path, wherein movement of the actuator in the upper position moves the diaphragm in the first chamber to the closed position to prevent flow of the composition.

In a second embodiment, a device is provided for delivering a pharmaceutical composition to a target tissue, the apparatus comprising: a syringe having a barrel, the barrel having a proximal end and a distal end, the barrel comprising a plunger being slidably receivable within the barrel to pressurize and expel the pharmaceutical composition contained in the barrel out the distal end of the barrel; a housing coupled to the distal end of the barrel of the syringe and configured to receive pressure and the composition from the barrel when the plunger is slid, the housing having an inlet, an outlet and a fluid path disposed therebetween, the fluid path in fluid communication with the inlet and the outlet; and a valve assembly disposed between the inlet and outlet and contacting the fluid path and having a chamber comprising a diaphragm movable in at least a closed position to prevent flow of the composition to the outlet and an actuator disposed in the chamber, the actuator responsive to pressure in the fluid path and coupled to the diaphragm in the chamber, the actuator movable in at least an upper position when a select pressure is reached in the fluid path, wherein movement of the actuator in the upper position moves the diaphragm in the chamber to the closed position to prevent flow of the composition.

In another embodiment, a method is provided for limiting or reducing pressure from a pharmaceutical composition on injection at or near a target tissue site, the method comprising injecting the pharmaceutical composition at or near the target tissue site using a syringe having a barrel, the barrel having a proximal end and a distal end, the barrel comprising a plunger being slidably receivable within the barrel to pressurize and expel the pharmaceutical composition contained in the barrel out the distal end of the barrel; a housing coupled to the distal end of the barrel of the syringe and configured to receive pressure and the composition from the barrel when the plunger is slid, the housing having an inlet, an outlet and a fluid path disposed therebetween, the fluid path in fluid communication with the inlet and the outlet, a valve assembly disposed between the inlet and outlet and contacting the fluid path and having a chamber comprising a diaphragm movable in at least a closed position to prevent flow of the composition to the outlet and an actuator disposed in the chamber, the actuator responsive to pressure in the fluid path and coupled to the diaphragm in the chamber, the actuator movable in at least an upper position when a select pressure is reached in the fluid path, wherein movement of the actuator in the upper position moves the diaphragm in the chamber to the closed position to prevent flow of the composition.

Additional features and advantages of various embodiments will be set forth in part in the description that follows, and in part will be apparent from the description, or may be learned by practice of various embodiments. The objectives and other advantages of various embodiments will be realized and attained by means of the elements and combinations particularly pointed out in the description and appended claims.

BRIEF DESCRIPTION OF THE FIGURES

In part, other aspects, features, benefits and advantages of the embodiments will be apparent with regard to the following description, appended claims and accompanying drawings where:

Figure 1:
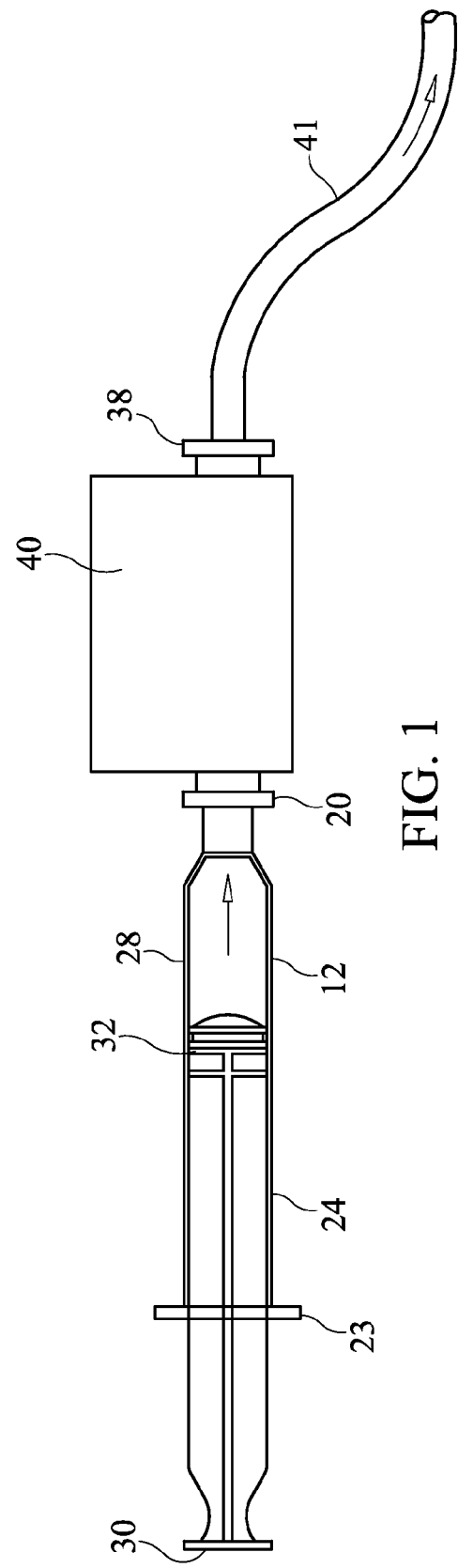
FIG. 1 illustrates a side plan view of an embodiment of a device for delivering a pharmaceutical composition to a target tissue site, where a syringe is coupled to a housing having the valve assembly, which is coupled to a delivery tube.

It is to be understood that the figures are not drawn to scale. Further, the relation between objects in a figure may not be to scale, and may in fact have a reverse relationship as to size. The figures are intended to bring understanding and clarity to the structure of each object shown, and thus, some features may be exaggerated in order to illustrate a specific feature of a structure.

DETAILED DESCRIPTION

For the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding the numerical ranges and parameters set forth herein, the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "1 to 10" includes any and all subranges between (and including) the minimum value of 1 and the maximum value of 10, that is, any and all subranges having a minimum value of equal to or greater than 1 and a maximum value of equal to or less than 10, e.g., 5.5 to 10.

Reference will now be made in detail to certain embodiments of the invention, examples of which are illustrated in the accompanying drawings. While the invention will be described in conjunction with the illustrated embodiments, it will be understood that they are not intended to limit the invention to those embodiments. On the contrary, the invention is intended to cover all alternatives, modifications, and equivalents that may be included within the invention as defined by the appended claims.

The headings below are not meant to limit the disclosure in any way; embodiments under any one heading may be used in conjunction with embodiments under any other heading.

DEFINITIONS

It is noted that, as used in this specification and the appended claims, the singular forms "a," "an," and "the," include plural referents unless expressly and unequivocally limited to one referent. Thus, for example, reference to "a chamber" includes one, two, three or more chambers.

The term "at or near" is intended to include a region extending up to and including from 0 cm to 5 cm from the target tissue site (e.g., nerve, muscle, ligament, bone, vertebra, etc.), as well as interior regions within the target tissue site.

The term "spine" includes neuronal, bony, vascular and soft tissue components. This includes the vertebral bodies and their associated joints (facets, costovertebral joints, or disc interfaces), the intervertebral discs, the intrinsic musculature, the spinal cord, spinal nerves, sympathetic nerves or ganglia associated with the axial skeleton, vertebral or disc innervations, and/or associated blood vessels.

The term "axial" refers to the head, neck and/or back of a patient.

The term "disc" may be one or more discs within a spinal column, including cervical, thoracic or lumbar discs.

The term "disc region" is intended to include a region extending about 5 cm from the surface of a disc, the surface of the disc, as well as interior regions within the disc.

The term "degeneration" refers to anatomical signs of degeneration, which can include changes in the height of the disc, the level of hydration of the disc, ruptured or contained herniation, annular bulging, and the presence of tearing or osteophytes. A reduction in the height of the disc may be one of the most common, early and easily detectable changes present in a degenerating disc. Another sign of degeneration is normally the loss of the T2 weighted signal on an MRI scan; this is indicative of a loss of hydration of the nuclear tissue. The degeneration can be a contained disc that occupies the space determined by the size of the endplates or a herniated disc. Herniation could be of a contained nature called, for example, bulging of the disc or a herniated disc can also be ruptured with release of discal elements, such as the nucleus pulposus, outside the disc. Signs of degeneration such as inflammation, tissue density, changes in pH, increased innervation and vascularization can also be found adjacent to the disc.

The term "surgical procedure" includes a procedure in which one or more incisions are made into the body in order to repair damage or remove diseased tissue.

The term "spinal surgery" includes a procedure in which one or more incisions are made and requires manipulation of spinal tissues, with or without removal and/or repair of spinal tissues. Examples of spinal surgery include, but are not limited to, repair of a herniated disc, adhesiolysis, radiofrequency neurotomy; intradiscal electrothermal therapy, fusion of vertebrae, full or partial discectomy, laminectomy, laminotomy, or laminoplasty, or the like.

The term "practitioner" means a person who is using the methods and/or devices of the current disclosure on the patient. This term includes, without limitation, doctors (e.g., surgeons, interventional specialists, physicians), nurses, nurse practitioners, other medical personnel, clinicians, veterinarians, or scientists.

The term "mammal" refers to organisms from the taxonomy class "mammalian," including but not limited to humans, other primates such as chimpanzees, apes, orangutans and monkeys, rats, mice, cats, dogs, cows, horses, etc. In various embodiments, the mammal is a human patient.

The term "fluid communication" includes that the pharmaceutical composition (e.g., liquid, solid, semi-solid) and/or pressure is in direct or indirect connection. Thus, for example, if the inlet is in fluid connection with the flow path, the connection may be through a direct connection, or through an indirect connection via other devices and connections.

The term "implantable" as utilized herein refers to a pharmaceutical composition (e.g., drug depot) retaining potential for successful placement within a mammal.

"Localized delivery" includes delivery of the pharmaceutical composition at or near the target tissue, for example, a nerve root of the nervous system or a region of the brain, or in close proximity (within about 5 cm, or preferably within about 2 cm, or within about 1 cm, or less for example) thereto. In some embodiments, localized delivery includes also delivering a drug depot locally to the target tissue site.

The term "pharmaceutical composition" as used herein is intended to have its broadest possible interpretation and is used to include any agent, or substance that when delivered to the body of a living being has a desired, usually beneficial, effect. Pharmaceutical substances include biologicals (.e.g., growth factors), drugs, carriers, tissue scaffolds, bulking material (e.g., bulking agents, sealers, in situ setting materials, gels, cements, etc.), or combinations thereof or the like.

Device for Delivery of the Composition

In some embodiments, a device is provided for delivering a pharmaceutical composition to a target tissue, the apparatus comprising: a syringe having a barrel, the barrel having a proximal end and a distal end, the barrel comprising a plunger being slidably receivable within the barrel to pressurize and expel the pharmaceutical composition contained in the barrel out the distal end of the barrel; a housing coupled to the distal end of the barrel of the syringe and configured to receive pressure and the composition from the barrel when the plunger is slid, the housing having an inlet, an outlet and a fluid path disposed therebetween, the fluid path in fluid communication with the inlet and the outlet; and a valve assembly disposed between the inlet and outlet and contacting the fluid path and having a chamber comprising a diaphragm movable in at least a closed position to prevent flow of the composition to the outlet and an actuator disposed in the chamber, the actuator responsive to pressure in the fluid path and coupled to the diaphragm in the chamber, the actuator movable in at least an upper position when a select pressure is reached in the fluid path, wherein movement of the actuator in the upper position moves the diaphragm in the chamber to the closed position to prevent flow of the composition.

FIG. 1 illustrates a side plan view of an embodiment of a device for delivering a pharmaceutical composition to a target tissue site, where a syringe 28 is coupled to a housing 40 having the valve assembly, which is coupled to a delivery tube 41.

The syringe 28 is generally cylindrical and has barrel 24 to hold and seal the pharmaceutical composition in a specific area within it at 12. The syringe has an opening near coupling 20 to allow the pharmaceutical composition to be expelled from it. The syringe has plunger 32 that when force is applied to it (manually or automatically) the plunger 32 slides longitudinally forward in the direction of coupling 20. The plunger will pressurize barrel 24 and the specific area 12 and expel the pharmaceutical composition into the housing 40 (having the valve assembly) out past coupling 38 to dispensing tube 41 and out to the target tissue site. This is provided that the maximum pressure for the injection is not reached. The syringe may have handle 30 to grasp and hold rim 23 as the practitioner slides the plunger 32 longitudinally forward to expel the pharmaceutical substance from the barrel 24 to expel it out past coupling 20 into housing 40. The housing 40, coupling 20 are in fluid communication with the barrel 24 and the housing 40 and housing coupling 38 are in fluid communication with flexible tubing 41. The housing coupling 20 can be any means including threading, reverse threading, mating pairs, leur fittings, etc. that allow the syringe to be coupled to the housing 40. Likewise, the housing coupling 38 can be any means including threading, reverse threading, mating pairs, leur fittings, etc. that allow the tube or needle or cannula to be coupled to the housing 40. The device of the present application can be all be in one unit pre-assembled or it can be assembled by taking a standard syringe and coupling it to housing 40 at coupling 20 and then a standard needle, cannula or tubing may be coupled to housing at 38 and the apparatus will be ready for delivery of the pharmaceutical composition.

The sidewall of the barrel 24 of the syringe 28 may be graduated or otherwise marked so as to gauge the position of the plunger 32 along the barrel.

In one embodiment, an injection shut off valve for reducing flow of a pharmaceutical composition is provided, the shut off valve comprising: a housing having an inlet, an outlet and a flow path disposed therebetween and in fluid communication with the inlet and the outlet, the inlet configured to receive an end of an injection syringe; and a valve assembly contacting the flow path and having a first chamber and a second chamber, the first chamber comprising a diaphragm movable in at least a closed position to prevent flow of the composition to the outlet, the second chamber having an actuator disposed therein, the actuator responsive to pressure in the flow path and coupled to the diaphragm in the first chamber, the actuator movable in at least an upper position when a select pressure is reached in the flow path, wherein movement of the actuator in the upper position moves the diaphragm in the first chamber to the closed position to prevent flow of the composition.

Figure 2A:
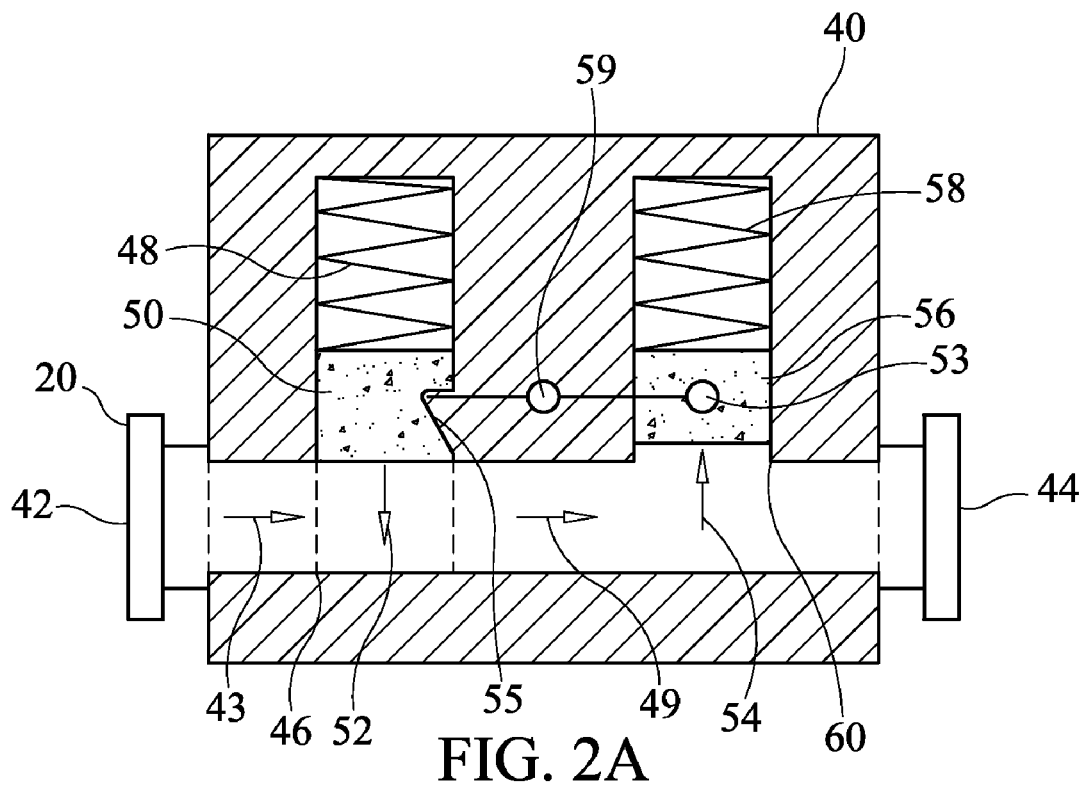
FIG. 2A illustrates a side cross sectional view of an embodiment of injection shut off valve assembly having a diaphragm in an open position and an actuator in a lower position that can connect to a syringe and/or cannula for delivery of the pharmaceutical composition.

FIG. 2A illustrates a side cross sectional view of an embodiment of injection shut off valve assembly having a diaphragm 50 shown in an open position and an actuator 56 in a lower position that can connect to a syringe and/or cannula (not shown) for delivery of the pharmaceutical composition. More particularly, the injection shut-off valve has a housing 40, inlet line 42 and outlet line 44. A flow path connecting inlet line 42 to outlet line 44 shown as 43 and 49 is disposed between the inlet line 42 and outlet line 44 and allows flow of the pharmaceutical composition (e.g., liquid, semi-solid, solid particles, etc.) to the outlet line 44, when certain pressure is reached in the valve assembly. For example, pressure generated from the practitioner sliding the plunger (32 in FIG. 1) in a forward direction increases the pressure in the barrel (24 in FIG. 1) to expel the pharmaceutical composition out beyond the coupling (20 in FIG. 1) and into inlet 42. The pharmaceutical composition will flow along flow path 43 when diaphragm 50 is in the open position as shown. Diaphragm 50 is in a first chamber 46 that contacts the flow path. The first chamber 46 has an elastic member 48 (e.g., spring, coil, clip, track, rib, sponge, wire, cable, projection, etc.) which biases against a surface of the diaphragm 50. When a select pressure is reached, the lever contacting the diaphragm at 55 is released and the elastic member will move the diaphragm 50 in the downward direction indicated by 52 to close the flow path and stop flow of the pharmaceutical composition and pressure.

Diaphragm 50 is configured to contact a pressure sensitive actuator 56 that is disposed in a second chamber 60 that also contacts the fluid path 49. In the embodiment shown, the diaphragm 50 and actuator 56 are substantially perpendicular to the fluid path. Also shown in the embodiment, the diaphragm comprises a recess 55 that is in contact with the actuator 56 via lever having pivot 59 and the lever contacts or is part of the actuator. Shown is the lever contacting the actuator 56 at hole 53. It will be understood by those of ordinary skill in the art that the diaphragm 50 may have one or more snap fit members, recesses, projections, wings, internal and external threading, tracks, clips, cleats, etc. that allow the lever to attach to the diaphragm and/or actuator.

The second chamber 60 has an elastic member 58 (e.g., spring, coil, clip, track, rib, sponge, wire, cable, projection, etc.) which biases against a surface of the actuator 56. The elastic member in both the first and second chambers can be set to a certain tension to allow movement of the actuator 56 in an upward direction shown by the arrow 54 depending on the pressure that is desired in the fluid path 49. The actuator 56 will move in the upward direction 54 when a certain pressure is reached. This will then cause the lever to release the diaphragm at recess 55 and the elastic member will expand and move the diaphragm 50 in the closed position stopping flow of pressure and the pharmaceutical composition.

For example, when injecting into a large vessel such as an artery, the diaphragm, lever, elastic member and/or actuator can be set to a larger pressure reflecting this type of injection site. In contrast, injection into a smaller vessel such as a vein or into a confined area, the diaphragm, lever, elastic member and/or actuator can be set to a lower pressure reflecting this type of injection site.

In some embodiments, as the pressure in the first or second chamber reaches greater than or equal to 80 psi, 90 psi, 100 psi, 110 psi, 120 psi, 130, psi, 140 psi, or 150 psi or higher, the diaphragm will move in the closed position and stop flow of the pharmaceutical composition.

In some embodiments, as the pressure in the needle or cannula tip reaches greater than or equal to 10 psi, 11 psi, 12 psi, 13 psi, 14 psi, 15 psi, 16 psi, 17 psi, 18 psi, 19 psi, or 20 psi or higher, the diaphragm will move in the closed position and stop flow of the pharmaceutical composition.

Figure 2B:
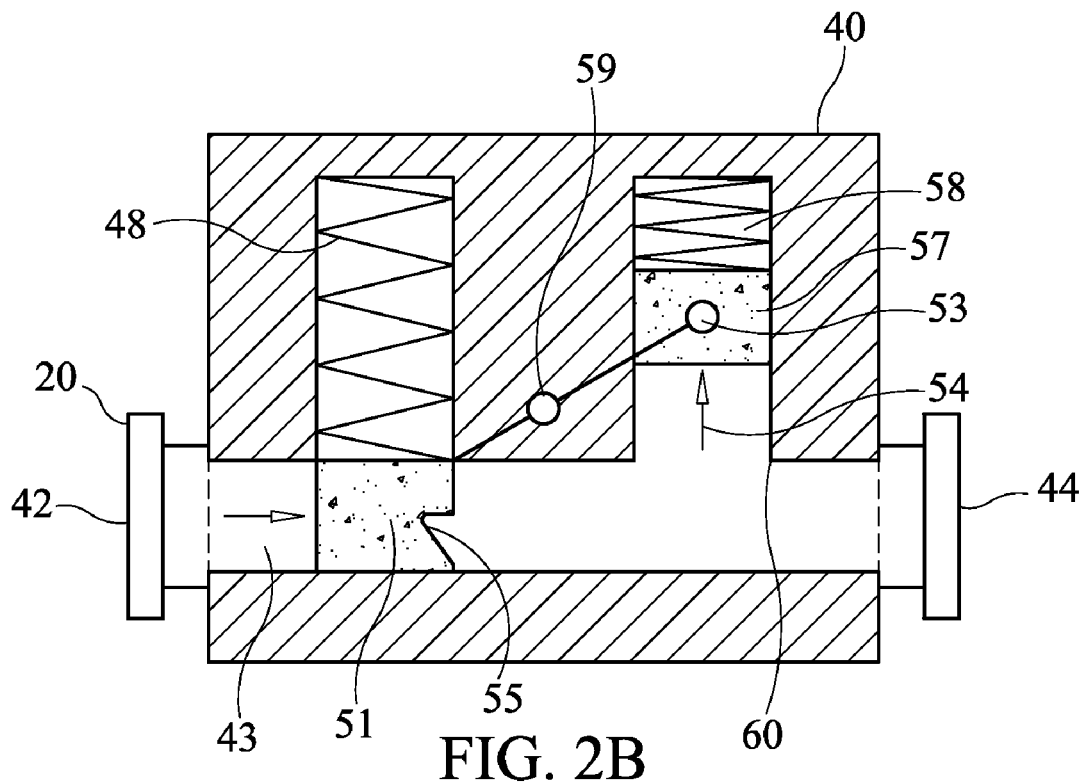
FIG. 2B illustrates a side cross sectional view of an embodiment of injection shut off valve assembly having a diaphragm in a closed position and an actuator in an upper position to prevent flow of the pharmaceutical composition.

FIG. 2B illustrates a side cross sectional view of an embodiment of injection shut off valve assembly when maximum pressure is reached in the flow path where the diaphragm 51 is shown in the closed position that prevents flow of the pharmaceutical composition out outlet 44 and an actuator 56 is moved in an upper position by the pressure and/or pharmaceutical composition. More particularly, the injection shut-off valve has a housing 40, inlet line 42 and outlet line 44. A flow path connecting inlet line 42 to outlet line 44 shown as 43 is disposed between them. As the pressure and/or pharmaceutical composition increases in the flow path by the second chamber 60 of the actuator, the actuator is moved in an upper position shown as 57 by the pressure and/or pharmaceutical composition (e.g., pressure from the liquid, semi-solid, solid particles, etc.) in the flow path. The arrow 54 shows the pressure and/or pharmaceutical composition moving the actuator up. The elastic member 58 is compressed by a surface of the actuator. The lever of the actuator at 53 has pivot 59 which releases the diaphragm in the first chamber at recess 55 causing elastic member 48 to expand and release diaphragm 51 into the flow path to prevent flow of the pharmaceutical composition and/or pressure in the flow path 43 and out outlet 44. The lever is shown in its released position. There will be a back up of pressure and/or pharmaceutical composition at the inlet 42 of the housing. The practitioner will detect the backup pressure as the plunger that is inside the syringe barrel that is coupled to the housing at 20 will be difficult to push. Therefore, as the maximum pressure is reached in the flow path the valve assembly will shut down and thus damage to tissue or leakage of the pharmaceutical composition to the surrounding tissue will be avoided.

In some embodiments, the diaphragm is smaller, the same size or larger than the flow path. In some embodiments, the diaphragm has the same diameter or a diameter that is larger than the flow path to stop flow of pressure and/or flow of the pharmaceutical composition in the flow path. In some embodiments, the actuator is the same size, smaller and/or larger than the flow path.

In some embodiments, the diaphragm comprises non-porous material to effectively seal the flow path 43 from pressure and/or pharmaceutical composition, when in the closed position. In some embodiments, the actuator 57 comprises non-porous material so that a more accurate measurement of pressure and/or pharmaceutical composition from the flow path 49 can be made. In some embodiments, the diaphragm and/or the actuator comprises non-deformable material.

Figure 3:
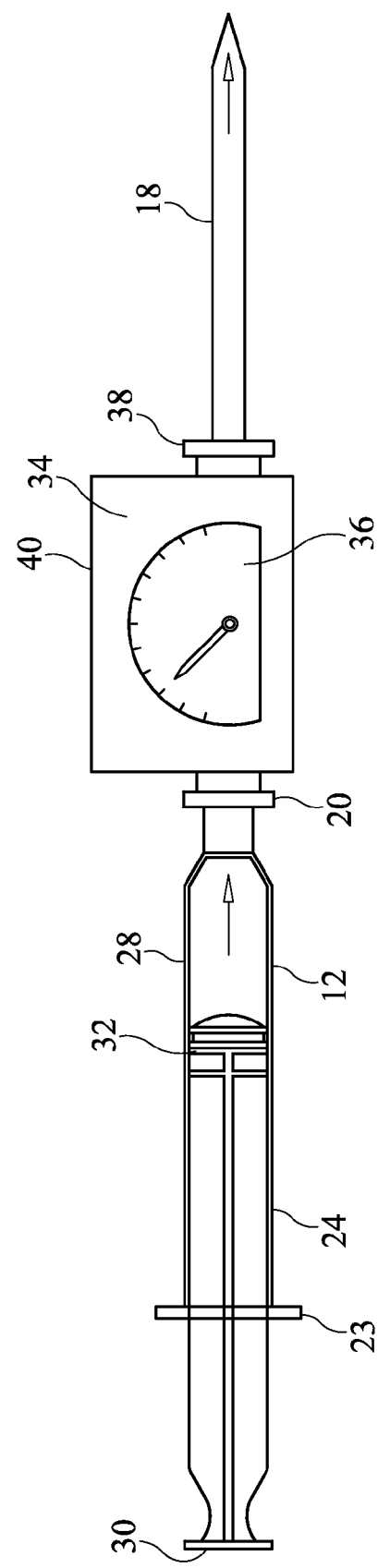
FIG. 3 illustrates a side plan view of an embodiment of a device for delivering a pharmaceutical composition to a target tissue site, where a syringe is coupled to a housing having the valve assembly, which is coupled to a delivery tube. The housing has a pressure gauge so that pressure from the injection can be monitored.

FIG. 3 illustrates a side plan view of an embodiment of a device for delivering a pharmaceutical composition to a target tissue site, where a syringe 28 is coupled to a housing 40 having the valve assembly, which is coupled to a delivery needle or cannula 18.

The syringe 28 is generally cylindrical and has barrel 24 to hold and seal the pharmaceutical composition in a specific area within it at 12. The syringe has an opening near coupling 20 to allow the pharmaceutical composition to be expelled from it. The syringe has plunger 32 that when force is applied to it (manually or automatically) the plunger 32 slides longitudinally forward in the direction of coupling 20. The plunger will pressurize barrel 24 and the specific area 12 and expel the pharmaceutical composition into the housing 40 (having the valve assembly and fluid path) out past coupling 38 to dispensing needle or cannula 41 and out to the target tissue site. This is provided that the maximum pressure for the injection is not reached.

The syringe may have handle 30, in manual injections, to grasp and hold rim 23 as the practitioner slides the plunger 32 longitudinally forward to expel the pharmaceutical substance from the barrel 24 to expel it through out past coupling 20 into housing 40. The housing 40, coupling 20 are in fluid communication with the barrel 24 and the housing 40 and housing coupling 38 are in fluid communication with needle or cannula 18. The housing coupling 20 can be any means including threading, reverse threading, mating pairs, leur fittings, etc. that allow the syringe to be coupled to the housing 40. Likewise, the housing coupling 38 can be any means including threading, reverse threading, mating pairs, leur fittings, etc. that allow the tube or needle or cannula to be coupled to the housing 40. The apparatus can be all be in one unit pre-assembled or it can be assemble by taking a standard syringe, loading it with the composition, and coupling it to housing 40 at coupling 20 and then a standard needle or tubing may be coupled to housing at 38 and the apparatus will be ready for delivery of the pharmaceutical composition.

A side wall of the housing 34 has pressure gauge 36 that indicates the pressure. The pressure gauge is coupled to the diaphragm, lever, elastic member and/or actuator so that as the pressure increases or decreases and there is movement of diaphragm, lever, elastic member and/or actuator, the pressure gauge will move as well and indicate the pressure in the fluid path. The pressure gauge can be calibrated beforehand according to an expected pressure to be met when the injection is indeed administered.

The sidewall of the barrel 24 of the syringe 28 may be graduated or otherwise marked so as to gauge the position of the plunger 32 along the barrel.

Figure 4A:
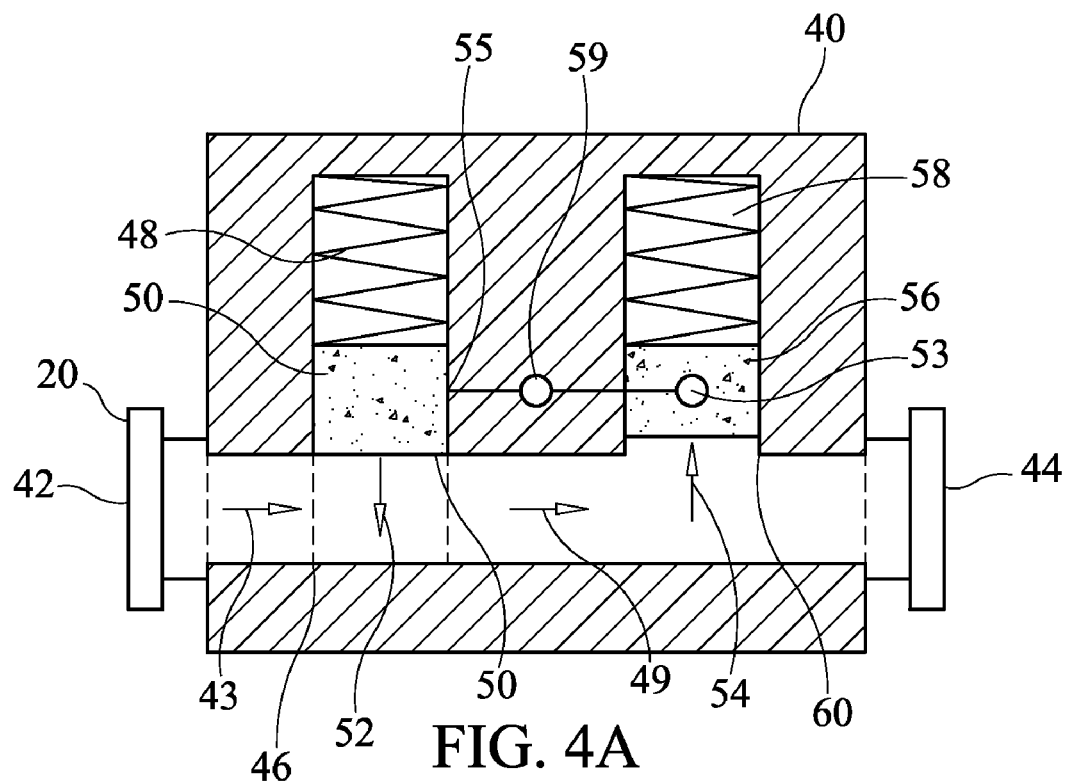
FIG. 4A illustrates a side cross sectional view of an embodiment of injection shut off valve assembly having a diaphragm in an open position and an actuator in a lower position that can connect to a syringe and/or cannula for delivery of the pharmaceutical composition.

FIG. 4A illustrates a side cross sectional view of an embodiment of injection shut off valve assembly having a diaphragm 50 shown in an open position and an actuator 56 in a lower position that can connect to a syringe and/or cannula (not shown) for delivery of the pharmaceutical composition. More particularly, the injection shut-off valve has a housing 40, inlet line 42 and outlet line 44. A flow path connecting inlet line 42 to outlet line 44 shown as 43 and 49 is disposed between the inlet line 42 and outlet line 44 and allows flow of the pharmaceutical composition (e.g., liquid, semi-solid, solid particles, etc.) to the outlet line 44, when certain pressure is reached in the valve assembly. For example, pressure generated from the practitioner sliding the plunger (32 in FIG. 1) in a forward direction increases the pressure in the barrel (24 in FIG. 1) to expel the pharmaceutical composition out passed the coupling (20 in FIG. 1) and into inlet 42. The pharmaceutical composition will flow along flow path 43 when diaphragm 50 is in the open position as shown. Diaphragm 50 is in a first chamber 46 that contacts the flow path. The first chamber 46 has an elastic member 48 (e.g., spring, coil, clip, track, rib, sponge, wire, cable, projection, etc.) which biases against a surface of the diaphragm 50. The elastic member will move the diaphragm 50 in the downward direction indicated by 52 to close the flow path and stop flow of the pharmaceutical composition and pressure. Diaphragm 50 is configured to contact a pressure sensitive actuator 56 that is disposed in a second chamber 60 that also contacts the fluid path 49. In the embodiment shown, the diaphragm 50 and actuator 56 are substantially perpendicular to the fluid path. Also shown in the embodiment, the diaphragm is in contact with the actuator 56 at contact point 55 via lever having pivot 59 (there is no recess in the diaphragm in this embodiment) and the lever contacts or is part of the actuator. Shown is the lever contacting the actuator 56 at hole 53. It will be understood by those of ordinary skill in the art that the diaphragm 50 may have one or more snap fit members, recesses, projections, wings, internal and external threading, tracks, clips, cleats, etc. that allow the lever to attach to the diaphragm and/or actuator. The second chamber 60 has an elastic member 58 (e.g., spring, coil, clip, track, rib, sponge, wire, cable, projection, etc.) which biases against a surface of the actuator 56. The elastic member in both the first and second chambers can be set to a certain tension to allow movement of the actuator 56 in an upward direction shown by the arrow 54 depending on the pressure that is desired in the fluid path 49. As the pressure and/or pharmaceutical composition increases in the flow path by the second chamber 60 of the actuator, the actuator is moved from a lower position to an upper position by the pressure and/or pharmaceutical composition (e.g., pressure from the liquid, semi-solid, solid particles, etc.) in the flow path. The arrow 54 shows the pressure and/or pharmaceutical composition moving the actuator up. The elastic member 58 is compressed by a surface of the actuator. The lever of the actuator at 53 has pivot 59 which moves the diaphragm in the first chamber at 55 causing elastic member 48 to expand and release diaphragm 50 into the flow path to prevent flow of the pharmaceutical composition and/or pressure in the flow path 43 and out outlet 44. The lever is shown in its unreleased position.

Figure 4B:
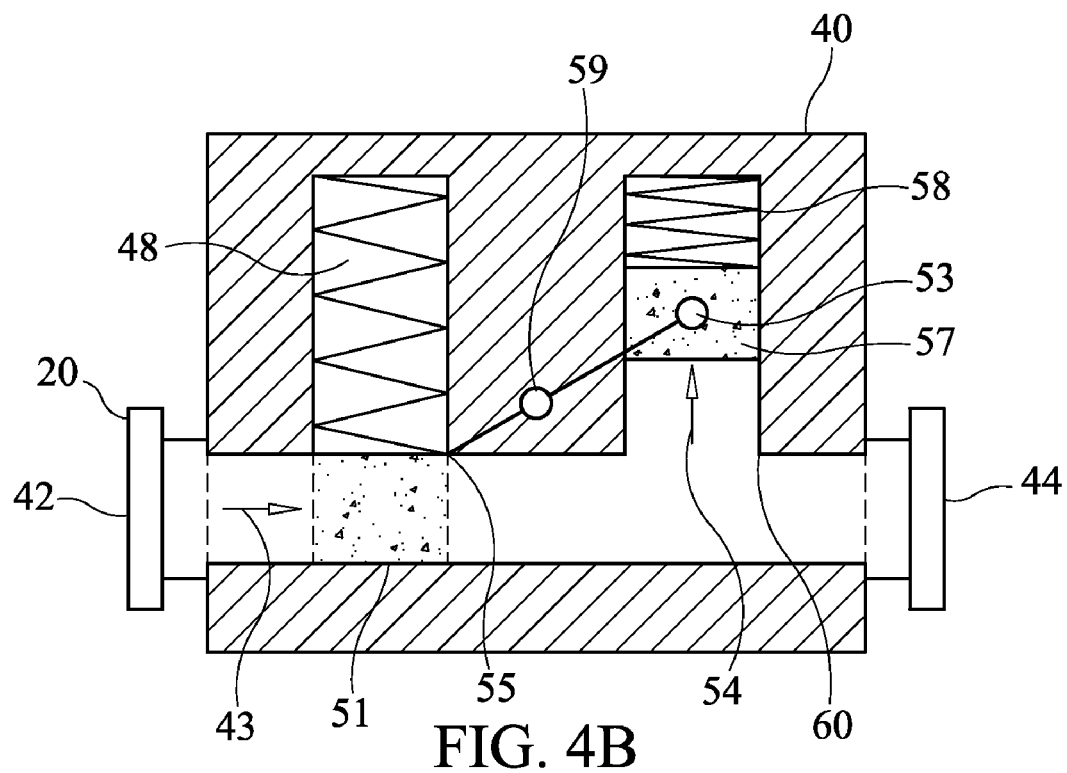
FIG. 4B illustrates a side cross sectional view of an embodiment of injection shut off valve assembly having a diaphragm in a closed position and an actuator in an upper position to prevent flow of the pharmaceutical composition.

FIG. 4B illustrates a side cross sectional view of an embodiment of injection shut off valve assembly when maximum pressure is reached in the flow path where the diaphragm 51 is shown in the closed position that prevents flow of the pharmaceutical composition out outlet 44 and an actuator 57 in an upper position. More particularly, the injection shut-off valve has a housing 40, inlet line 42 and outlet line 44. A flow path connecting inlet line 42 to outlet line 44 shown as 43 is disposed between them. As the pressure and/or pharmaceutical composition increases in the flow path by the second chamber 60 of the actuator, the actuator is moved in an upper position shown as 57 by the pressure and/or pharmaceutical composition (e.g., pressure from the liquid, semi-solid, solid particles, etc.) in the flow path. The arrow 54 shows the pressure and/or pharmaceutical composition moving the actuator up. The elastic member 58 is compressed by a surface of the actuator. The lever of the actuator at 53 has pivot 59 which assists in moving the diaphragm in the first chamber at 55 causing elastic member 48 to expand and move diaphragm 51 into the flow path to prevent flow of the pharmaceutical composition and/or pressure in the flow path 43 and out outlet 44. The lever is shown in its released position. There will be a back up of pressure and/or pharmaceutical composition. The practitioner will detect the backup pressure as the plunger that is inside the syringe barrel that is coupled to the housing at 20 will be difficult to push. Therefore, as the maximum pressure is reached in the flow path the valve assembly will shut down and thus damage to tissue or leakage of the pharmaceutical composition to the surrounding tissue will be avoided.

In the embodiments shown in FIGS. 4A and 4B, the lever 59 contacts the diaphragm in such a way that as pressure increases, the diaphragm will move gradually in increments downward and the actuator will move in the reciprocal direction (increments upward in response to the increased pressure). In this way the flow of the pharmaceutical composition will gradually decrease in increments as pressure in the fluid path increases. If pressure exceeds the maximum pressure the diaphragm 51 will completely block the fluid path and flow will stop.

Likewise, in the embodiments shown in FIGS. 4A and 4B, the lever 59 contacts the diaphragm in such a way that as pressure decreases, the diaphragm will move in increments upward and the actuator will move in the reciprocal direction (increments downward in response to the decreased pressure). In this way, the flow of the pharmaceutical composition will gradually increase in increments as pressure in the fluid path decreases.

Figure 5:
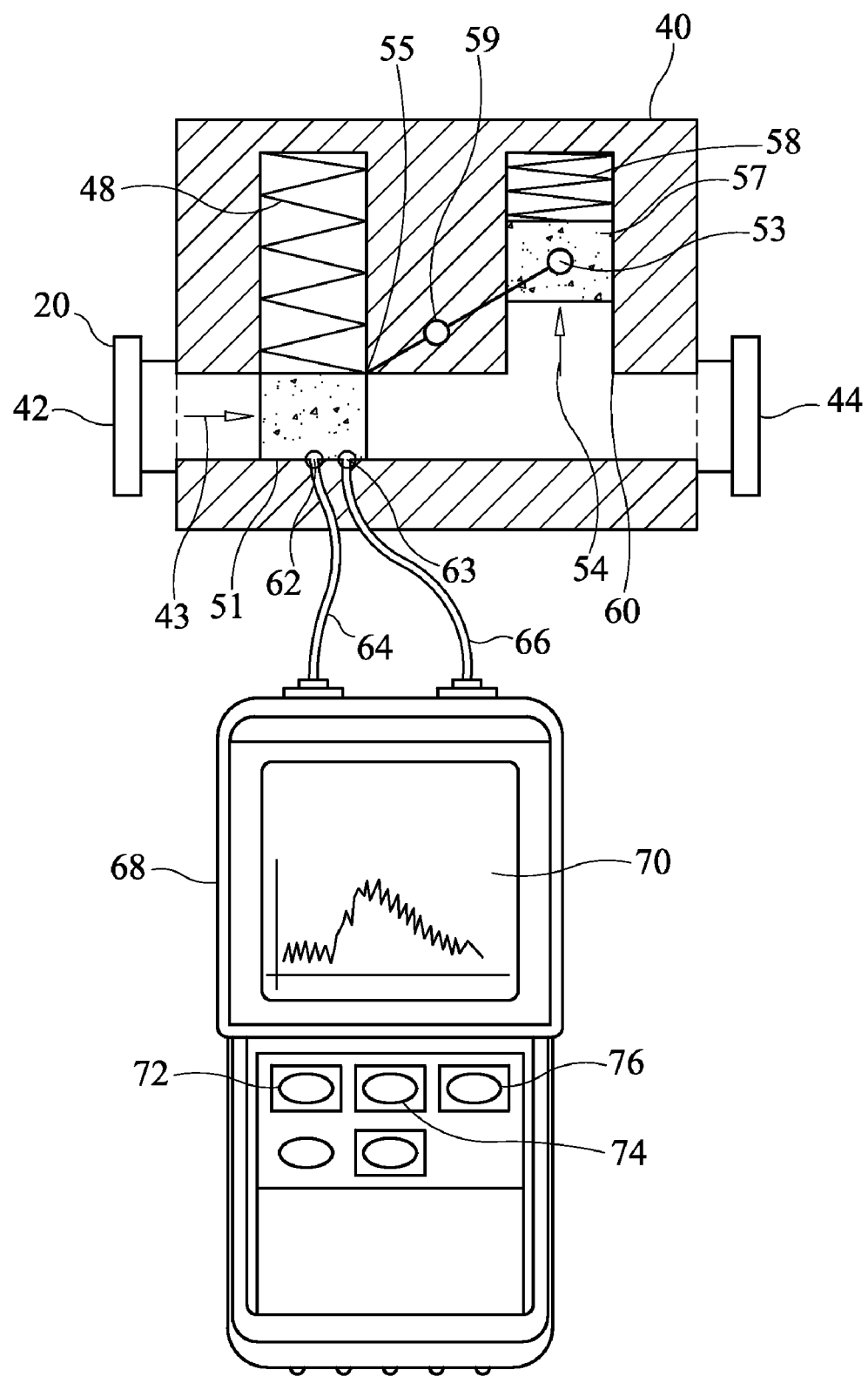
FIG. 5 illustrates a side cross sectional view of an embodiment of injection shut off valve assembly having a diaphragm in a closed position and an actuator in an upper position to prevent flow of the pharmaceutical composition. Here the valve assembly is coupled to a computerized displayed to measure pressure.

FIG. 5 illustrates a side cross sectional view of an embodiment of injection shut off valve assembly when maximum pressure is reached in the flow path where the diaphragm 51 is shown in the closed position that prevents flow of the pharmaceutical composition out outlet 44 and an actuator 57 in an upper position. In this embodiment, a computer 68 is coupled to the diaphragm so that as the pressure increases or decreases and there is movement of diaphragm, the pressure display 70 will indicate the pressure in the fluid path.

More particularly, the injection shut-off valve has a housing 40, inlet line 42 and outlet line 44. A flow path connecting inlet line 42 to outlet line 44 shown as 43 is disposed between them. As the pressure and/or pharmaceutical composition increases in the flow path by the second chamber 60 of the actuator, the actuator is moved in an upper position shown as 57 by the pressure and/or pharmaceutical composition (e.g., pressure from the liquid, semi-solid, solid particles, etc.) in the flow path. The arrow 54 shows the pressure and/or pharmaceutical composition moving the actuator up. The elastic member 58 is compressed by a surface of the actuator. The lever of the actuator at 53 has pivot 59 which assists in moving the diaphragm in the first chamber at 55 causing elastic member 48 to expand and move diaphragm 51 in a downward direction into the flow path to prevent flow of the pharmaceutical composition and/or pressure in the flow path 43 and out outlet 44. The lever is shown in its released position. There will be a back up of pressure and/or pharmaceutical composition when the diaphragm 51 is in the closed portion.

In the embodiments shown in FIG. 5, the diaphragm has two electrical contact points 62 and 63, which contact two electrical leads 64 and 66 coupled to computer 68. As the two contact points 62 and 63 of diaphragm 51 contacts the electrical contact points, a pulse is generated in electrical leads 64 and 66 to generate a pulse as shown in pressure display 70. The practitioner will notice the peak in the display 70 and know that maximum pressure in the flow path has been reached and the injection and flow of the pharmaceutical will stop. It will be understood by those of ordinary skill in the art that one of more electrical contact points leading to the computer and display can be disposed anywhere in the housing, for example, in the lever, elastic member, flow path and/or actuator, as long as data can be sent to the computer 68 and shown on display 70. The computer may have data entry keys 72 to calibrate the pressure sensitive actuator 57. There may be also be data entry keys 74 to select the desired pressure that if exceeded will cause the diaphragm to seal the flow path and prevent delivery of the pharmaceutical composition. There also may be data entry keys to shut the apparatus off 76 or turn it on.

In some embodiments, the pressure for activation of the actuator and to stop flow can be set depending on factors, such as for example, the type of composition, the duration of the injection, type of treatment, and the type of tissue the cannula, needle, or tube will be placed at or near. For example, the device can be set so that low pressure and/or pharmaceutical composition is given to the target tissue site at or near the spine (e.g., annulus, nucleus, facet capsule, nerve root, etc.).

In the embodiment shown in FIG. 5, the lever 59 contacts the diaphragm in such a way that as pressure increases, the diaphragm will move gradually in increments downward and the actuator will move in the reciprocal direction (increments upward in response to the increased pressure). In this way the flow of the pharmaceutical composition will gradually decrease in increments as pressure in the fluid path increases. If pressure exceeds the maximum pressure the diaphragm 51 will completely block the fluid path and flow will stop. Likewise, in the embodiments shown in FIG. 5, the lever 59 contacts the diaphragm in such a way that as pressure decreases, the diaphragm will move in increments upward and the actuator will move in the reciprocal direction (increments downward in response to the decreased pressure). In this way, the flow of the pharmaceutical composition will gradually increase in increments as pressure in the fluid path decreases. The pressure can be monitored on display 70. Although the computer display is shown in FIG. 5 as separate, it will be understood by those of ordinary skill in the art that the computer display can be one single unit and on one side of the housing 40.

The device for injecting the pharmaceutical composition comprises a cannula, needle and/or tubing that can be inserted through the skin to a target tissue site at or near the spine (e.g., at an area comprising at least one muscle, ligament, tendon, cartilage near the spine, or spinal nerve, spinal disc, spinal foraminal space near the spinal nerve root, facet or spinal canal). One advantage of the embodiments provided herein is that by utilizing an injection shut off valve that prevents flow of the pharmaceutical composition when a maximum pressure is reached, the practitioner can administer the composition where the risk of damage to the tissue resulting from high pressure injections is reduced or eliminated. For example, when treating a spinal disc herniation, the practitioner will often administer anti-inflammatory compositions at or near the site of the disc herniation. If the anti-inflammatory composition is administered under excessive pressure, this can cause further trauma to the disc area by causing the nucleus pulposus to leak out of the annulus fibrosus leading to further herniation and/or painful debilitating effects on the patient by compressing the spinal canal and spinal nerve root. By using the present apparatus, injections that exceed a safe pressure are prevented as the diaphragm would prevent such pressure from reaching the target tissue site to cause the further tissue damage.

The cannula or needle or tubing of the device is designed to cause minimal physical and psychological trauma to the patient. Cannulas or needles include tubes that may be made from materials, such as for example, polyurethane, polyurea, polyether(amide), PEBA, thermoplastic elastomeric olefin, copolyester, and styrenic thermoplastic elastomer, steel, aluminum, stainless steel, titanium, metal alloys with high non-ferrous metal content and a low relative proportion of iron, carbon fiber, glass fiber, plastics, ceramics or combinations thereof. The cannula or needle or tube may optionally include one or more tapered regions. In various embodiments, the cannula or needle or tube may be beveled. The cannula or needle or tube may also have a tip style vital for accurate treatment of the patient depending on the anatomical site. Examples of tip styles include, for example, Trephine, Cournand, Veress, Huber, Seldinger, Chiba, Francine, Bias, Crawford, deflected tips, Hustead, Lancet, or Tuohey. In various embodiments, the cannula or needle or tube may also be non-coring and have a sheath covering it to avoid unwanted needle sticks.

In some embodiments, the cannula or needle or tube of the delivery device has a diameter that is the same size or smaller than the diameter of at least part of the plunger. In various embodiments, the diameter of the cannula or needle or tubing is substantially the same throughout. In other embodiments, the diameter of the needle or cannula becomes smaller approaching the distal end for delivery of the composition.

In some embodiments the cannula, needle, or tube is flexible. The flexibility of the cannula, needle, or tube allows the device to be maneuvered along a bend in the target tissue (e.g., the spine, muscle, joint, etc.). The flexibility of the cannula, needle, or tube allows the injection locally to the target tissue site and is often dictated by anatomical consideration.

The dimensions of the hollow cannula or needle or tubing, among other things, will depend on the anatomic site for treatment. For example, the width of the epidural space is only about 3-5 mm for the thoracic region and about 5-7 mm for the lumbar region. Thus, the needle or cannula or tubing, in various embodiments, can be designed for these specific areas. In various embodiments, the needle, cannula or tubing may be inserted using a transforaminal approach in the spinal foramen space, for example, along an inflamed nerve root and the pharmaceutical composition injected at this site for treating the condition. Typically, the transforaminal approach involves approaching the intervertebral space through the intervertebral foramina and injecting the pharmaceutical composition.

Some examples of lengths of the cannula or needle or tube may include, but are not limited to, from about 50 to 150 mm in length, for example, about 65 mm for epidural pediatric use, about 85 mm for a standard adult and about 110 mm for an obese adult patient. The thickness of the cannula or needle will also depend on the site of implantation. In various embodiments, the thickness includes, but is not limited to, from about 0.05 to about 1.655. The gauge of the cannula or needle may be the widest or smallest diameter or a diameter in between for insertion into a human or animal body. The widest diameter is typically about 14 gauge, while the smallest diameter is about 22 gauge. In various embodiments the gauge of the needle or cannula is about 18 to about 22 gauge.

The housing including elastic member, lever, diaphragm, actuator, flow path, inlet, and outlet can be made from materials, such as for example, polyurethane, polyurea, polyether (amide), PEBA, thermoplastic elastomeric olefin, copolyester, and styrenic thermoplastic elastomer, steel, aluminum, stainless steel, titanium, metal alloys with high non-ferrous metal content and a low relative proportion of iron, carbon fiber, glass fiber, plastics, ceramics or combinations thereof. The housing may optionally include one or more tapered regions to assist in coupling the barrel and/or cannula, needle, and/or tube thereto.

In some embodiments, the syringe includes a barrel and a plunger. The plunger has a diameter less than the barrel so that it can be slidably received therein. The plunger may be longer, shorter, the same size, or smaller in length than the cannula or needle or tubing. Like the housing, the plunger and barrel may be made from materials, such as for example, polyurethane, polyurea, polyether(amide), PEBA, thermoplastic elastomeric olefin, copolyester, and styrenic thermoplastic elastomer, steel, aluminum, stainless steel, titanium, metal alloys with high non-ferrous metal content and a low relative proportion of iron, carbon fiber, glass fiber, plastics, ceramics or combinations thereof.

The delivery device may be part or coupled to imaging devices used for radiography, fluoroscopy, luminescence, PET, SPECT, CT, MRI, and/or X-ray imaging techniques and display images as the cannula, needle, or tube is inserted at or near the target tissue site (e.g., at an area comprising at least one muscle, ligament, tendon, cartilage near the spine, or spinal nerve, spinal disc, spinal foraminal space near the spinal nerve root, facet, annulus, or spinal canal, etc.).

Pharmaceutical Composition

The term "pharmaceutical composition" as used herein is intended to have its broadest possible interpretation and is used to include any agent, or substance that when delivered to the body of a living being has a desired, usually beneficial, effect. Pharmaceutical substances include biologicals (.e.g., growth factors), drugs, carriers, tissue scaffolds, bulking material (e.g., bulking agents, sealers, in situ setting materials, gels, cements, etc.), or combinations thereof or the like.

In various embodiments, the barrel, housing, cannula, needle, and/or tubing comprises a liquid, solid, or semi-solid pharmaceutical composition that can be injected at the target tissue site. The pharmaceutical composition is flowable. For example, the pharmaceutical composition can be a flowable powder, liquid, or semi-solid (e.g., gel).

In some embodiment, the device limits the pressure that is allowed to be injected at, near or in a tissue. For example, when dealing with painful degenerating intervertebral discs, the device will limit the pressure from flowable compositions such as silk, elastin, polyurethane, fibrin sealant, polyvinyl alcohol, sealants, in situ setting materials, cements, etc., which have no drugs but bulk up the disc to both increase disc stability and seal any annular tears. If the practitioner injects with too much pressure further damage can occur. The present device limits the pressure on injection and thus the risk of a highly pressurized injection is eliminated or reduced.

Representative classes of pharmaceutical compositions that can be used in the present device include, e.g., trophic factors, analgesics, anti-inflammatory agents, anti-cancer agents, vaccines, adjuvants, antibodies, neuroleptics, genes and genetic elements for transfection including viral vectors for gene therapy, cells or cellular components, etc. A list of more specific examples would therefore include, collagen, insoluble collagen derivatives, etc., soluble solids and/or liquids dissolved therein, e.g., antiviricides, antimicrobials such as erythromycin, bacitracin, neomycin, penicillin, polymicin B, tetracyclines, biomycin, chloromycetin, and streptomycins, cephalosporins, ampicillin, azactam, tobramycin, clindamycin and gentamicin, etc.; biocidal/biostatic sugars such as dextran, glucose, etc.; amino acids, peptides, vitamins, inorganic elements, co-factors for protein synthesis; hormones; endocrine tissue or tissue fragments, synthesizers; enzymes such as collagenase, peptidases, oxidases, etc., polymer cell scaffolds with parenchymal cells, angiogenic drugs, polymeric carriers containing such drugs; collagen lattices; antigenic agents; cytoskeletal agents; cartilage fragments, modified living cells such as chondrocytes, bone marrow cells, mesenchymal stem cells, natural extracts, genetically engineered living cells or otherwise modified living cells, DNA delivered by plasmid or viral vectors, genes or genetic elements, tissue transplants, demineralized bone powder, autogenous tissues such as blood, serum, soft tissue, bone marrow, bone substitutes, bone cements, etc.; bioadhesives; non-collagenous proteins such as osteoponfin, osteonectin, bone sialo protein, laminin, fibrinogen, vitronectin, thrombospondin, proteoglycans, decorin, beta glycan, biglycan, aggrecan, versican, tenascin, matrix gla protein, hyaluronan, amino acids, amino acid residues, peptides, bone morphogenic proteins (BMPs); osteoinductive factor (OIF); fibronectin (FN); endothelial cell growth factor (ECGF); cementum attachment extracts (CAE); ketanserin; human growth hormone (HGH); animal growth hormones; epidermal growth factor (EGF); interleukin-1 (IL-1); human alpha thrombin; transforming growth factor (TGF-beta); insulin-like growth factor (IGF-1) (IGF-2); platelet derived growth factors (PDGF); fibroblast growth factors (FGF, aFGF, bFGF, etc.); periodontal ligament chemotactic factor (PDLGF); somatotropin; bone digestors; antitumor agents; immunosuppressants; fatty acids (including polar and non-polar fatty acids); permeation enhancers, e.g., fatty acid esters such as laureate, myristate and stearate monoesters of polyethylene glycol, enamine derivatives, alpha-keto-aldehydes, etc.; and nucleic acids; inorganic elements, inorganic compounds, cofactors for protein synthesis, hormones, soluble and insoluble components of the immune system; soluble and insoluble receptors including truncated forms; soluble, insoluble and cell surface bound ligands including truncated forms; chemokines, bioactive compounds that are endocytosed; endocrine tissue or tissue fragments, growth factor binding proteins, e.g., insulin-like growth factor binding protein (IGFBP-2) (IGFBP-4) (IGFBP-5) (IGFBP-6); angiogenic agents, bone promoters, cytokines, interleukins, genetic material, genes encoding bone promoting actions, cells containing genes encoding bone promoting action; growth hormones such as somatotrophin; bone digestors; antitumor agents; cellular attractants and attachment agents; immuno suppressants; bone resorption inhibitors and stimulators; angiogenic and mitogenic factors; bioactive factors that inhibit and stimulate secondary messenger molecules; cell adhesion molecules, e.g., cell-matrix and cell-cell adhesion molecules; secondary messengers, monoclonal antibodies specific to cell surface determinants on mesenchymal stem cells, clotting factors; externally expanded autograft or xenograft cells, nucleic acids or any combinations thereof.

The pharmaceutical composition that the device can deliver can be a bulking or sealing agent. A wide variety of biocompatible polymeric materials may be used as the bulking agent and/or sealing agent, including, but not limited to, silicon, polyurethane, copolymers of silicon and polyurethane, polyolefins, such as polyisobutylene and polyisoprene, neoprene, nitrile, polyvinyl alcohol, acrylamides such as polyacrylic acid and poly(acrylonitrile-acrylic acid), non-biologically absorbable polyurethanes, polyethylene glycol, poly(N-vinyl-2-pyrrolidone), acrylates such as polyacrylates, poly(2-hydroxy ethyl methacrylate), methyl methacrylate, 2-hydroxyethyl methacrylate, and copolymers of acrylates with N-vinyl pyrrolidone, N-vinyl lactams, acrylamide, polyurethanes and polyacrylonitrile, glycosaminoglycans, collagen, polyethylene oxide, co-polymers of PVA and PVP, and combinations thereof. These materials may further be cross-linked to provide further strength. Examples of polyurethanes include thermoplastic polyurethanes, aliphatic polyurethanes, segmented polyurethanes, hydrophilic polyurethanes, polyether-urethane, polycarbonate-urethane and silicon polyether-urethane. Other suitable hydrophilic polymers include naturally-occurring materials such as glucomannan gel, polyphosphazenes, hyaluronic acid, polysaccharides, such as cross-linked carboxyl-containing polysaccharides, alkyl celluloses, hydroxyalkyl methyl celluloses, sodium chondroitin sulfate, cyclodextrin, polydextrose, dextran, gelatin, and combinations thereof. Other suitable examples of biologically acceptable polymers include biocompatible homopolymers and copolymers of hydrophilic monomers such as 2-hydroxyalkyl acrylates and methacrylates, N-vinyl monomers, and ethylenically unsaturated acids and bases; polycyanoacrylate, polyethylene oxide-polypropylene glycol block copolymers, polygalacturonic acid, polyvinyl pyrrolidone, polyvinyl acetate, polyalkylene glycols, polyethylene oxide, collagen, sulfonated polymers, vinyl ether monomers or polymers, alginate, polyvinyl amines, polyvinyl pyridine, and polyvinyl imidazole.

One can also use superabsorbent polymers (SAP) with or without additives. Superabsorbent polymers may include polymer chains that are synthetic, natural, and hybrid synthetic/natural polymers. Exemplary superabsorbent polymers may include, but are not limited to, polyacrylic acid, polymethacrylic acid, polymaleic acid, copolymers thereof, and alkali metal and ammonium salts thereof; graft copolymers of starch and acrylic acid, starch and saponified acrylonitrile, starch and saponified ethyl acrylate, and acrylate-vinyl acetate copolymers saponified; polyvinylpyrrolidone, polyvinyl alkylether, polyethylene oxide, polyacrylamide, and copolymers thereof; copolymers of maleic anhydride and alkyl vinylethers; saponified starch graft copolymers of acrylonitrile, acrylate esters, vinyl acetate, and starch graft copolymers of acrylic acid, methyacrylic acid, and maleic acid; the product of crosslinking acrylamide with backbones of kappa-carrageenan and soldium alginate using methylenebisacrylamide and potassium persulfate; and the product of crosslinking, using a bifunctional crosslinking reagent, an acyl-modified protein matrix such as soy protein isolate which has been acyl-modified by treatment with ethylenediaminetetraacetic acid dianhydride; mixtures and combinations thereof. Further, one can use silicon-based materials, polyethylene terephthalate, polycarbonate, thermoplastic elastomers and copolymers such as ether-ketone polymers such as polyetheretherketone or a combination thereof. In some embodiments, the bulking and/or sealing agent can include any hydrostatic and/or hemostatic agents for sealing, (e.g., gelfoam), tissues, and/or proteins including collagen. In some embodiments, the bulking and/or sealing agent can be a superabsorbent polymer (SAP). The SAP can be cross-linked to enhance its absorbency capacity and gel strength. Superabsorbent polymers may include polymer chains that are synthetic, natural, and hybrid synthetic-natural polymers. Natural polymers include polysaccharides such as cellulose, starch, and regenerated cellulose that are modified to be carboxylated, phosphonoalkylated, sulphoxylated or phosphorylated, thereby causing the polymer chains to become highly hydrophilic. Synthetic polymers that can be used as SAP include, but are not limited to, polyacrylates. U.S. Pat. No. 5,147,343, U.S. Pat. No. 4,673,402, U.S. Pat. No. 5,281,207, and U.S. Pat. No. 4,834,735 disclose many types of SAPs and methods for making them, and are incorporated herein by reference in their entirety in accordance with the described embodiments.

In some embodiments, suitable bulking and/or sealing agents include crosslinkable macromonomers that form hydrogels. These bulking and/or sealing agents macromers have a backbone of a polymer having units with a 1,2-diol and/or 1,3-diol structure. Such polymers include poly(vinyl alcohol) (PVA) and hydrolyzed copolymers of vinyl acetate, for example, copolymers with vinyl chloride, N-vinylpyrrolidone, etc. The backbone polymer may contain pendant chains bearing crosslinkable groups and, optionally, other modifiers. When crosslinked, the macromers form hydrogels advantageous for use as bulking and/or sealing agents for different tissue types. Specific examples of bulking and/or sealing agents include microspheres formed from macromers, wherein the macromers prior to crosslinking have a polymeric backbone comprising units with a 1,2-diol or 1,3-diol structure and at least two pendant chains bearing crosslinkable groups which are olefinically unsaturated groups, wherein the macromers are crosslinked via free radical polymerization to form a hydrogel. These types of polymeric bulking and/or sealing agents are described in U.S. Pat. No. 6,652,883 and U.S. Pat. No. 7,070,809, assigned to BioCure, Inc. The entire disclosures of these patents are incorporated by reference herein.

Suitable bulking and/or sealing agents include a hydrogel formed from a macromer having a polymeric backbone comprising units with a 1,2-diol or 1,3-diol structure and at least two pendant chains bearing crosslinkable groups and an amphiphilic comonomer. The hydrogel can have a yield load between about 1000 to 6000 Newtons or a compression modulus of approximately 3 mega pascals at 10-30% strain and the comonomer can be diacetone acrylamide (DAA), N-vinyl caprolactam, N-(butoxymethyl)acrylamide, N-acroyl morpholine, crotonamide, N,N-dimethyl acrylamide, N-octadecylacrylamide, acrylamide or a combination thereof. The hydrogel can have a macromer having a poly (vinyl alcohol) backbone with a molecular weight of about 14,000 and the pendant chains bearing crosslinkable groups are N-acrylamidoacetaldehyde dimethyl acetal (NAAADA) in an amount of about 6 to 21 crosslinkers per PVA. These types of polymeric bulking and/or sealing agents are described in U.S. Ser. No. 11/170,915, filed Jun. 29, 2005 and published as US 2005/0288789 assigned to BioCure, Inc. The entire disclosure of this patent application is incorporated by reference herein.

Suitable bulking and/or sealing agents can comprise macromers having a backbone comprising a polymeric backbone having units with a 1,2-diol or 1,3-diol structure, such as polyvinyl alcohol, and pendant chains bearing crosslinkable groups and, optionally, other modifiers. When crosslinked, the macromers form hydrogels that can seal and fill lumens and spaces, such as in an intervertebral disc. In some embodiments, the bulking and/or sealing agent can be crosslinked and form microspheres. In some embodiments, the polymeric backbone comprises a polyhydroxy polymer and the pendant chains bearing crosslinkable groups are attached to the backbone via the 1,2-diol or 1,3-diol groups. In some embodiments, the pendant chains bearing crosslinkable groups are attached to the backbone via cyclic acetal linkages. These types of polymeric bulking and/or sealing agents are described in U.S. Pat. No. 6,676,971, and U.S. Pat. No. 6,710, 126, assigned to BioCure, Inc. These entire disclosures of these patents are incorporated by reference herein.

Suitable bulking and/or sealing agents can comprise polymerizable carbohydrate esters and polymers therefrom and homo- and co-polymers having monomers with hydrophilic, amphiphilic or hydrophobic properties that are able to form hydrogels, as described in U.S. Pat. No. 5,571,882. The entire disclosure of this patent is incorporated by reference herein.

Suitable bulking and/or sealing agents can include membranes made from amphiphilic copolymers. The amphiphilic copolymers can be ABA copolymers, where one of A and B is hydrophilic and the other is hydrophobic. The copolymers may be crosslinked to form more stable structures. Crosslinking can be accomplished using a variety of methods, including end to end polymerization of copolymers having terminal unsaturated groups as described in U.S. Pat. No. 6,723,814. The entire disclosure of this patent is incorporated by reference herein.

Suitable bulking and/or sealing agents can be delivered to the site in situ at or near the damaged tissue and then gel in situ to form a hydrogel. These bulking and/or sealing agents include macromers having water soluble regions and crosslinkable regions as described in U.S. Ser. No. 09/960, 449, filed Sep. 21, 2001 and published as US 2002/0122771. This entire disclosure of this patent application is incorporated by reference herein.

The bulking and/or sealing agents can be incorporated into polymeric hollow particles for delivery that change permeability in response to a change in an external stimulus such as pH, temperature, light, ionic strength, electric field, magnetic field and/or solvent composition. The hollow particles can have a shell formed of an amphiphilic triblock ABA or BAB copolymer, where A is a hydrophilic block and B is a hydrophobic block, as described in U.S. Pat. No. 6,616,946, assigned to BioCure, Inc. The entire disclosure of this patent is incorporated by reference herein.

In some embodiments, the pharmaceutical composition comprises a carrier matrix for implantation in a bone defect. The carrier matrix, when placed in a bone defect, provides scaffolding around which the patient's new bone will grow, gradually replacing the carrier matrix as the target site heals. Examples of suitable carrier matrices may include, but are not limited to, the MasterGraft® Matrix produced by Medtronic Sofamor Danek, Inc., Memphis, Tenn.; MasterGraft® Putty produced by Medtronic Sofamor Danek, Inc., Memphis, Tenn.; Absorbable Collagen Sponge ("ACS") produced by Integra LifeSciences Corporation, Plainsboro, N.J.; bovine skin collagen fibers coated with hydroxyapatite, e.g. Healos® marketed by Johnson & Johnson, USA; collagen sponges, e.g. Hemostagene® marketed by Coletica SA, France, or e.g. Helisat® marketed by Integra Life Sciences Inc., USA; and Collagraft® Bone Graft Matrix produced by Zimmer Holdings, Inc., Warsaw, Ind. These carrier matrices can be modified to be flowable for use in the device.

In some embodiments, the pharmaceutical composition comprises one or more known members of the BMP family including, but not limited to, BMP-1, BMP-2, BMP-3, BMP-4, BMP-5, BMP-6, BMP-7, BMP-8, BMP-9, BMP-10, BMP-11, BMP-12, BMP-13, BMP-15, BMP-16, BMP-17, BMP-18 as well as polynucleotides or polypeptides thereof, as well as mature polypeptides or polynucleotides encoding the same.

In various embodiments, the pharmaceutical composition can comprise a drug depot. A "drug depot" is the composition in which at least one anti-inflammatory agent and/or at least one analgesic agent or the pharmaceutically acceptable salts of either or both are administered to the body. Thus, a drug depot may comprise a physical structure to facilitate implantation and retention in a desired site (e.g., a disc space, a spinal canal, a tissue of the patient, particularly at or near a site of surgery, pain, or site of inflammation, etc.). The drug depot also comprises the drug itself. The term "drug" as used herein is generally meant to refer to any substance that alters the physiology of a patient. The term "drug" may be used interchangeably herein with the terms "therapeutic agent," "therapeutically effective amount," and "active pharmaceutical ingredient" or "API."

It will be understood that unless otherwise specified a "drug" formulation may include more than one therapeutic agent, wherein exemplary combinations of therapeutic agents include a combination of two or more drugs. The drug provides a concentration gradient of the therapeutic agent for delivery to the site. In various embodiments, the drug depot provides an optimal drug concentration gradient of the therapeutic agent at a distance of up to about 0.1 cm to about 5 cm from the implant site, and comprises at least one anti-inflammatory agent or its pharmaceutically acceptable salt and/or at least one analgesic agent or its pharmaceutically acceptable salt.

A "depot" includes but is not limited to capsules, microspheres, microparticles, microcapsules, microfibers particles, nanospheres, nanoparticles, coating, matrices, wafers, pills, pellets, emulsions, liposomes, micelles, gels, or other pharmaceutical delivery compositions or a combination thereof. Suitable materials for the depot are ideally pharmaceutically acceptable biodegradable and/or any bioabsorbable materials that are preferably FDA approved or GRAS materials. These materials can be polymeric or non-polymeric, as well as synthetic or naturally occurring, or a combination thereof.

In some embodiment, the pharmaceutical composition comprises an analgesic or an anti-inflammatory agent. The phrase "anti-inflammatory agent" refers to an agent or compound that has anti-inflammatory effects. These agents may remedy pain by reducing inflammation. Anti-inflammatory agents also include those agents in a different classification with anti-inflammatory properties, such as, for example, amitriptyline, carbamazepine, gabapentin, pregabalin, clonidine, or other alpha adrenergic receptor agonist or a combination thereof.

A "therapeutically effective amount" or "effective amount" is such that when administered, the pharmaceutical composition results in alteration of the biological activity, such as, for example, inhibition of inflammation, reduction or alleviation of pain, improvement in the condition, etc. The dosage administered to a patient can unless otherwise specified or apparent from context be as single or multiple doses depending upon a variety of factors, including the pharmaceutical composition's administered pharmacokinetic properties, the route of administration, patient conditions and characteristics (sex, age, body weight, health, size, etc.), extent of symptoms, concurrent treatments, frequency of treatment and the effect desired. In some embodiments the pharmaceutical composition is designed for immediate release. In other embodiments the pharmaceutical composition is designed for sustained release. In other embodiments, the pharmaceutical composition comprises one or more immediate release surfaces and one or more sustain release surfaces.

In some embodiments, the pharmaceutical composition comprises one or more antimicrobials, antibiotics, antimyobacterial, antifungals, antivirals, antineoplastic agents, antitumor agents, agents affecting the immune response, blood calcium regulators, agents useful in glucose regulation, anticoagulants, antithrombotics, antihyperlipidemic agents, cardiac drugs, thyromimetic and antithyroid drugs, adrenergics, antihypertensive agents, cholnergics, anticholinergics, antispasmodics, antiulcer agents, skeletal and smooth muscle relaxants, prostaglandins, general inhibitors of the allergic response, antihistamines, local anesthetics, analgesics, narcotic antagonists, antitussives, sedative-hypnotic agents, anticonvulsants, antipsychotics, anti-anxiety agents, antidepressant agents, anorexigenlcs, non-steroidal anti-inflammatory agents, steroidal anti-inflammatory agents, antioxidants, vaso-active agents, bone-active agents, osteogenic factors, osteoinductive factors, antiarthritics, diagnostic agents or a combination thereof.

In various embodiments, the pharmaceutical composition can be administered by injection. Injection includes administration that is intravenous, intramuscular, through continuous or intermittent infusion, intraperitoneal, intrasternal, subcutaneous, intra-operatively, intrathecally, intradiskally, peridiskally, epidurally, perispinally, intra-articularly or a combination thereof. Injection also includes administration of a pharmaceutical composition in a immediate release or bolus dose or sustained or controlled release delivery.

In various embodiments, the device described herein is packaged in a kit. The kit may include additional parts along with the device, for example, disposable cannulas, drug depots, etc. The kit may include a syringe, needle, cannula and/or tube in one compartment and the housing containing the valve assembly. The third compartment may include the pharmaceutical composition, gloves, drapes, wound dressings and other procedural supplies for maintaining sterility, as well as an instruction booklet and a DVD showing how the device operates. A fourth compartment may include additional cannulas and/or needles. Each tool may be separately packaged in a plastic pouch that is radiation sterilized. A fifth compartment may include an agent for radiographic imaging. A cover of the kit may include illustrations of the ultrasonic probe procedure and a clear plastic cover may be placed over the compartments to maintain sterility.

Methods

In some embodiments, a method is provided for limiting or reducing pressure from a pharmaceutical composition on injection at or near a target tissue site, the method comprising injecting the pharmaceutical composition at or near the target tissue site using a syringe having a barrel, the barrel having a proximal end and a distal end, the barrel comprising a plunger being slidably receivable within the barrel to pressurize and expel the pharmaceutical composition contained in the barrel out the distal end of the barrel; a housing coupled to the distal end of the barrel of the syringe and configured to receive pressure and the composition from the barrel when the plunger is slid, the housing having an inlet, an outlet and a fluid path disposed therebetween, the fluid path in fluid communication with the inlet and the outlet, a valve assembly disposed between the inlet and outlet and contacting the fluid path and having a chamber comprising a diaphragm movable in at least a closed position to prevent flow of the composition to the outlet and an actuator disposed in the chamber, the actuator responsive to pressure in the fluid path and coupled to the diaphragm in the chamber, the actuator movable in at least an upper position when a select pressure is reached in the fluid path, wherein movement of the actuator in the upper position moves the diaphragm in the chamber to the closed position to prevent flow of the composition.

In some embodiments, the devices and methods described herein are utilized in the diagnosis and treatment of vertebral abnormalities, such as, compression fractures, pars defects, vertebral instability, soft tissue abnormalities in ligaments, tendons, annulus, muscles, cartilaginous structures, joints (e.g., facet joints, intervertebral discs, sacroiliac joints, etc.) or abnormalities resulting from tumors, infection or other infiltrative processes, nerve root lesions (e.g., compressive lesions from adjacent discs, hypertrophic facet joints, facet joints cysts, faulty hardware positioning, bony foraminal encroachment, spondylolisthesis, spondylolysis, congenitally short pedicles, nerve sheath tumors, granulation tissue and/or arachnoiditis, etc.), spinal nerve compression (e.g., spinal stenosis), peripheral nerve lesions, femoral neuropathy, meralgia paresthetica, peroneal neuropathy, asymmetrical neuropathies, lower limb joint pathology, vascular pathology, degenerative disc and joint disease or the like.

In some embodiments, the devices and methods of the current application can be used to treat conditions including rheumatoid arthritis, osteoarthritis, spinal disc annular tear or herniation (e.g., sciatica), carpal/tarsal tunnel syndrome, lower back pain, discogenic back pain, lower extremity pain, upper extremity pain, cancer, tissue pain and pain associated with injury or repair of cervical, thoracic, and/or lumbar vertebrae or intervertebral discs, rotator cuff, articular joint, TMJ, tendons, ligaments, muscles, spondilothesis, stenosis, or joint pain or the like.

In some embodiments, the devices and methods described herein are utilized in the diagnosis and treatment of back pain from, for example, a herniated disc, or spinal stenosis. Typically, when a patient has a herniated disc, the patient will exhibit severe or persistent radicular pain. When the herniated disc is in the lower back, persistent pain can originate in the back and often extends ("radiates") into the leg along the distribution of the sciatic nerve (lumbar radicular pain, or sciatica). In patients with herniated disc in the neck, the persistent pain can originate in the neck and often radiates into the arm. The devices and methods of the present application can assist the practitioner in diagnosing and providing treatment for such condition.

Spinal stenosis is another condition where the patient will exhibit, among other things, back pain. Spinal stenosis, either acquired or congenital, results from degenerative changes in the spine, variably including the intervertebral disks, the intervertebral joints (facet joints) and the ligamentum flavum. In each case, the degenerative changes together result in a gradual narrowing of the lumbar or cervical spinal canal, causing compression of the spinal cord and spinal nerve roots. Symptoms include: pain and/or numbness in the neck, back, buttocks, legs, thighs or calves that is worse with walking, standing and/or exercise; back pain that radiates to the legs; weakness of the legs; and difficulty or imbalance when walking. Patients can be diagnosed with spinal stenosis through, for example, persistent radiating pain; neurologic examination findings of abnormal sensation and muscle weakness in the legs; gait disturbances and characteristic bent over posture; asymmetric deep tendon reflexes; and radiologic findings of spinal stenosis by x-ray (e.g., myelogram), MRI, spinal CT or CT myelography or the like. Depending on whether the stenosis is central or foraminal, provocative maneuvers on physical examination such as side bending reproducing the pain may be negative or positive, respectively. The devices and methods of the present application can assist the practitioner in diagnosing and providing treatment for such condition.

It will be apparent to those skilled in the art that various modifications and variations can be made to various embodiments described herein without departing from the spirit or scope of the teachings herein. Thus, it is intended that various embodiments cover other modifications and variations of various embodiments within the scope of the present teachings.

What is claimed is:

1. An injection shut off valve for limiting flow of a composition, the shut off valve comprising:
   a housing having an inlet, an outlet and a flow path disposed therebetween and in fluid communication with the inlet and the outlet, the inlet configured to receive an end of an injection syringe; and
   a valve assembly contacting the flow path and having a first chamber and a second chamber, the first chamber comprising a diaphragm movable in at least a closed position to prevent flow of the composition to the outlet, the second chamber having an actuator disposed therein, the actuator responsive to pressure in the flow path and coupled to the diaphragm in the first chamber, the actuator movable in at least an upper position when a select pressure is reached in the flow path, wherein movement of the actuator in the upper position moves the diaphragm in the first chamber to the closed position to prevent flow of the composition, and the actuator further comprises a lever that contacts the diaphragm and releases the diaphragm when the actuator is moved in the upper position to prevent flow to the outlet.

2. An injection shut off valve according to claim 1, wherein the diaphragm and actuator are substantially perpendicular to the flow path.

3. An injection shut off valve according to claim 1, wherein the select pressure does not exceed a maximum pressure that causes damage to a tissue of a patient.

4. An injection shut off valve according to claim 1, wherein the inlet is connected to a syringe containing the composition that is a liquid, or semisolid and the outlet is connected to a needle, cannula or flexible tubing.

5. An injection shut off valve according to claim 1, wherein the diaphragm is movable in an open position to allow flow to the outlet when the actuator is in a lower position and the pressure in the flow path is less than the select pressure.

6. An injection shut off valve according to claim 1, wherein (i) the diaphragm has a surface that contacts an elastic member disposed in the first chamber that holds the diaphragm in the closed position to prevent flow of the composition or (ii) the actuator has a surface that contacts an elastic member disposed in the second chamber that pushes the actuator in a lower position moving the diaphragm in an open position to allow flow of the composition.

7. An injection shut off valve according to claim 1, wherein the diaphragm moves incrementally to the closed position to prevent flow to the outlet.

8. An injection shut off valve according to claim 1, wherein the diaphragm and/or actuator is coupled to a gauge having indicators to measure the pressure.

9. A device for delivering a pharmaceutical composition to a target tissue, the apparatus comprising:
   a syringe having a barrel, the barrel having a proximal end and a distal end, the barrel comprising a plunger being slidably receivable within the barrel to pressurize and expel the pharmaceutical composition contained in the barrel out the distal end of the barrel;
   a housing coupled to the distal end of the barrel of the syringe and configured to receive pressure and the composition from the barrel when the plunger is slid, the housing having an inlet, an outlet and a fluid path disposed therebetween, the fluid path in fluid communication with the inlet and the outlet; and
   a valve assembly disposed between the inlet and outlet and contacting the fluid path and having a first chamber comprising a diaphragm movable in at least a closed position to prevent flow of the composition to the outlet and an actuator disposed in a second the chamber, the actuator responsive to pressure in the fluid path and coupled to the diaphragm in the first chamber, the actuator movable in at least an upper position when a select pressure is reached in the fluid path, wherein movement of the actuator in the upper position moves the diaphragm in the first chamber to the closed position to prevent flow of the composition, wherein the actuator further comprises a lever that contacts the diaphragm and releases the diaphragm when the actuator is moved in the upper position to prevent flow to the outlet.

10. A device according to claim 9, wherein the diaphragm and actuator are substantially perpendicular to the fluid path.

11. A device according to claim 9, wherein the select pressure does not exceed a maximum pressure that causes damage to the target tissue of a patient.

12. A device according to claim 9, wherein the outlet is connected to a needle, cannula or flexible tubing.

13. A device according to claim 9, wherein the diaphragm is smaller, the same size or larger than the diameter of the fluid path and the diaphragm is movable in an open position to allow the composition to flow to the outlet, when the actuator is in a lower position and the pressure is lower than the select pressure.

14. A device according to claim 9, wherein (i) the diaphragm contacts an elastic member disposed in the first chamber that holds the diaphragm in the closed position to prevent flow of the composition or (ii) the actuator contacts an elastic member disposed in the first chamber that pushes the actuator in a lower position moving the diaphragm in an open position to allow flow of the composition.

15. A device according to claim 9, wherein (i) the diaphragm moves incrementally to the closed position to prevent the composition flow to the outlet; or (ii) the diaphragm and/or actuator is coupled to a gauge having indicators to measure the pressure.

16. A device according to claim 9, wherein the pharmaceutical composition comprises a liquid, solid, or semisolid.

17. A method for limiting pressure from a pharmaceutical composition on injection at or near a target tissue site, the method comprising injecting the pharmaceutical composition at or near the target tissue site using a syringe having a barrel, the barrel having a proximal end and a distal end, the barrel comprising a plunger being slidably receivable within the barrel to pressurize and expel the pharmaceutical composition contained in the barrel out the distal end of the barrel; a housing coupled to the distal end of the barrel of the syringe and configured to receive pressure and the composition from the barrel when the plunger is slid, the housing having an inlet, an outlet and a fluid path disposed therebetween, the fluid path in fluid communication with the inlet and the outlet, a valve assembly disposed between the inlet and outlet and contacting the fluid path and having a first chamber comprising a diaphragm movable in at least a closed position to prevent flow of the composition to the outlet and an actuator disposed in a second chamber, the actuator responsive to pressure in the fluid path and coupled to the diaphragm in the first chamber, the actuator movable in at least an upper position when a select pressure is reached in the fluid path, wherein movement of the actuator in the upper position moves the diaphragm in the first chamber to the closed position to prevent flow of the composition, and the actuator further comprises a lever that contacts the diaphragm and releases the diaphragm when the actuator is moved in the upper position to prevent flow to the outlet.

18. A method according to claim 17, wherein a needle or cannula is coupled to the outlet of the housing.

19. A method according to claim 17, wherein (i) the pharmaceutical composition comprises a liquid, solid, or semisolid; or (ii) the target tissue site is an intervertebral disc; or (iii) the pressure on injection does not exceed (iii) about 100 to about 140 psi or (iv) 120 psi or (v) about 10 to about 20 psi in a needle or cannula that is coupled to the outlet of the housing.

20. An injection shut off valve for limiting flow of a composition, the shut off valve comprising:
  a housing having an inlet, an outlet and a flow path disposed therebetween and in fluid communication with the inlet and the outlet, the inlet configured to receive an end of an injection syringe; and
  a valve assembly contacting the flow path and having a first chamber and a second chamber, the first chamber comprising a diaphragm movable in at least a closed position to prevent flow of the composition to the outlet, the second chamber having an actuator disposed therein, the actuator responsive to pressure in the flow path and coupled to the diaphragm in the first chamber, the actuator movable in at least an upper position when a select pressure is reached in the flow path, wherein movement of the actuator in the upper position moves the diaphragm in the first chamber to the closed position to prevent flow of the composition and the diaphragm and actuator are substantially perpendicular to the flow path.

21. An injection shut off valve according to claim 20, wherein the select pressure does not exceed a maximum pressure that causes damage to a tissue of a patient.

22. An injection shut off valve according to claim 20, wherein the inlet is connected to a syringe containing the composition that is a liquid, or semisolid and the outlet is connected to a needle, cannula or flexible tubing.

23. An injection shut off valve according to claim 20, wherein the diaphragm is movable in an open position to allow flow to the outlet when the actuator is in a lower position and the pressure in the flow path is less than the select pressure.

24. An injection shut off valve according to claim 20, wherein the diaphragm moves incrementally to the closed position to prevent flow to the outlet.

25. An injection shut off valve according to claim 20, wherein the diaphragm and/or actuator is coupled to a gauge having indicators to measure the pressure.

* * * * *

UNITED STATES PATENT AND TRADEMARK OFFICE
CERTIFICATE OF CORRECTION

PATENT NO.         : 7,955,301 B1
APPLICATION NO.    : 12/694329
DATED              : June 7, 2011
INVENTOR(S)        : McKay It is certified that error appears in the above-identified patent and that said Letters Patent is hereby corrected as shown below:

In Column 19, Line 57, delete "cholnergics," and insert -- cholinergics, --, therefor.

In Column 19, Line 63, delete "anorexigenlcs," and insert -- anorexigenics, --, therefor.

In Column 24, Line 9, in Claim 19, delete "(iii) the" and insert -- the --, therefor.

Signed and Sealed this
Twenty-sixth Day of July, 2011

David J. Kappos
*Director of the United States Patent and Trademark Office*